United States Patent
Chowaniec et al.

(10) Patent No.: US 9,023,014 B2
(45) Date of Patent: May 5, 2015

(54) QUICK CONNECT ASSEMBLY FOR USE BETWEEN SURGICAL HANDLE ASSEMBLY AND SURGICAL ACCESSORIES

(75) Inventors: Matthew J. Chowaniec, Middletown, CT (US); Xingrui Chen, Hamden, CT (US); Michael A. Zemlok, Prospect, CT (US)

(73) Assignee: Covidien LP, Mansfield, MA (US)

(*) Notice: Subject to any disclaimer, the term of this patent is extended or adjusted under 35 U.S.C. 154(b) by 198 days.

(21) Appl. No.: 13/543,979

(22) Filed: Jul. 9, 2012

(65) Prior Publication Data
US 2012/0323226 A1    Dec. 20, 2012

Related U.S. Application Data

(60) Continuation-in-part of application No. 13/484,975, filed on May 31, 2012, which is a continuation-in-part of application No. 13/331,047, filed on Dec. 20, 2011, now Pat. No. 8,968,276, which is a (Continued)

(51) Int. Cl.
*A61B 17/29* (2006.01)
*A61B 17/072* (2006.01)
(Continued)

(52) U.S. Cl.
CPC ....... *A61B 17/072* (2013.01); *A61B 2017/2931* (2013.01); *A61B 17/115* (2013.01); *A61B 2017/0023* (2013.01); *A61B 2017/00371* (2013.01); *A61B 2017/00398* (2013.01);
(Continued)

(58) Field of Classification Search
USPC ............................................................ 606/1
See application file for complete search history.

(56) References Cited

U.S. PATENT DOCUMENTS

| | | | |
|---|---|---|---|
| 4,722,685 | A | 2/1988 | de Estrada et al. |
| 4,823,807 | A | 4/1989 | Russell et al. |

(Continued)

FOREIGN PATENT DOCUMENTS

| | | | |
|---|---|---|---|
| AU | 2008229795 A1 | 4/2009 | |
| CA | 2451558 | 1/2003 | |

(Continued)

OTHER PUBLICATIONS

Extended European Search Report corresponding to EP 13 17 5377.4, completed Jul. 30, 2013, and mailed Aug. 6, 2013; (5 pp).

(Continued)

*Primary Examiner* — Aaron Roane

(57) ABSTRACT

A hand-held electromechanical surgical device is provided and configured to selectively connect with a surgical accessory. The surgical device includes a device housing defining a connecting portion for selectively receiving a coupling assembly of the surgical accessory. The connecting portion includes an annular wall defining a cylindrical recess dimensioned to receive the coupling assembly of the surgical accessory; a collar slidably supported about the annular wall, wherein the collar is slidable between a first position and a second position; and at least one socket member interposed between the annular wall and the collar, wherein each socket member is slidably supported in the annular wall. Each socket member includes a first fixed state wherein each socket member projects into the cylindrical recess of the annular wall; and a second movable state wherein each socket member is free to not project into the cylindrical recess of the annular wall.

13 Claims, 8 Drawing Sheets

Related U.S. Application Data continuation-in-part of application No. 12/946,082, filed on Nov. 15, 2010, now Pat. No. 8,806,973, said application No. 13/331,047 is a continuation-in-part of application No. 12/758,900, filed on Apr. 13, 2010, which is a continuation-in-part of application No. 12/622,827, filed on Nov. 20, 2009, said application No. 13/331,047 is a continuation-in-part of application No. 13/089,672, filed on Apr. 19, 2011, now Pat. No. 8,342,379, which is a division of application No. 12/235,362, filed on Sep. 22, 2008, now Pat. No. 7,963,433, said application No. 13/331,047 is a continuation-in-part of application No. 13/089,473, filed on Apr. 19, 2011, said application No. 13/331,047 is a continuation-in-part of application No. 13/090,286, filed on Apr. 20, 2011, now Pat. No. 8,272,554.

(60) Provisional application No. 61/308,045, filed on Feb. 25, 2010, provisional application No. 61/265,942, filed on Dec. 2, 2009, provisional application No. 60/974,267, filed on Sep. 21, 2007.

(51) Int. Cl.
  *A61B 17/115*     (2006.01)
  *A61B 17/00*      (2006.01)

(52) U.S. Cl.
  CPC .................. *A61B2017/00464* (2013.01); *A61B 2017/00473* (2013.01)

(56) References Cited

U.S. PATENT DOCUMENTS

| | | | |
|---|---|---|---|
| 5,301,061 A | 4/1994 | Nakada et al. | |
| 5,411,508 A | 5/1995 | Bessler et al. | |
| 5,427,087 A | 6/1995 | Ito et al. | |
| 5,507,297 A * | 4/1996 | Slater et al. | 600/564 |
| 5,540,375 A | 7/1996 | Bolanos et al. | |
| 5,540,706 A | 7/1996 | Aust et al. | |
| 5,632,432 A | 5/1997 | Schulze et al. | |
| 5,658,300 A | 8/1997 | Bito et al. | |
| 5,693,042 A | 12/1997 | Boiarski et al. | |
| 5,762,603 A | 6/1998 | Thompson | |
| 5,782,396 A | 7/1998 | Mastri et al. | |
| 6,010,054 A | 1/2000 | Johnson et al. | |
| 6,032,849 A | 3/2000 | Mastri et al. | |
| 6,126,651 A | 10/2000 | Mayer | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,371,909 B1 | 4/2002 | Hoeg et al. | |
| 6,459,822 B1 | 10/2002 | Hathaway et al. | |
| 6,471,637 B1 | 10/2002 | Green et al. | |
| 6,645,218 B1 | 11/2003 | Cassidy et al. | |
| 6,654,999 B2 | 12/2003 | Stoddard et al. | |
| 6,783,533 B2 | 8/2004 | Green et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,905,057 B2 | 6/2005 | Swayze et al. | |
| 6,986,451 B1 | 1/2006 | Mastri et al. | |
| 6,988,649 B2 | 1/2006 | Shelton, IV et al. | |
| RE39,152 E | 6/2006 | Aust et al. | |
| 7,059,508 B2 | 6/2006 | Shelton, IV et al. | |
| 7,122,029 B2 | 10/2006 | Koop et al. | |
| 7,140,528 B2 | 11/2006 | Shelton, IV | |
| 7,147,138 B2 | 12/2006 | Shelton | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,407,078 B2 | 8/2008 | Shelton, IV et al. | |
| 7,481,824 B2 | 1/2009 | Boudreaux et al. | |
| 7,565,993 B2 | 7/2009 | Milliman et al. | |
| 7,575,144 B2 | 8/2009 | Ortiz et al. | |
| 7,699,835 B2 | 4/2010 | Lee et al. | |
| 7,793,812 B2 | 9/2010 | Moore et al. | |
| 7,822,458 B2 | 10/2010 | Webster, III et al. | |
| 7,845,534 B2 | 12/2010 | Viola et al. | |
| 7,857,185 B2 | 12/2010 | Swayze et al. | |
| 7,870,989 B2 | 1/2011 | Viola et al. | |
| 7,922,719 B2 | 4/2011 | Ralph et al. | |
| 7,947,034 B2 | 5/2011 | Whitman | |
| 7,954,682 B2 | 6/2011 | Giordano et al. | |
| 7,959,051 B2 | 6/2011 | Smith et al. | |
| 7,967,179 B2 | 6/2011 | Olson et al. | |
| 8,016,178 B2 | 9/2011 | Olson et al. | |
| 8,025,199 B2 | 9/2011 | Whitman et al. | |
| 8,052,024 B2 | 11/2011 | Viola et al. | |
| 8,114,118 B2 | 2/2012 | Knodel et al. | |
| 8,132,705 B2 | 3/2012 | Viola et al. | |
| 8,152,516 B2 | 4/2012 | Harvey et al. | |
| 8,157,150 B2 | 4/2012 | Viola et al. | |
| 8,182,494 B1 | 5/2012 | Yencho et al. | |
| 8,186,587 B2 | 5/2012 | Zmood et al. | |
| 8,235,273 B2 | 8/2012 | Olson et al. | |
| 8,272,554 B2 | 9/2012 | Whitman et al. | |
| 8,292,150 B2 | 10/2012 | Bryant | |
| 8,342,379 B2 | 1/2013 | Whitman et al. | |
| 8,353,440 B2 | 1/2013 | Whitman et al. | |
| 8,365,633 B2 | 2/2013 | Simaan et al. | |
| 8,371,492 B2 | 2/2013 | Aranyi et al. | |
| 8,424,739 B2 | 4/2013 | Racenet et al. | |
| 8,454,585 B2 | 6/2013 | Whitman | |
| 8,505,802 B2 | 8/2013 | Viola et al. | |
| 8,517,241 B2 | 8/2013 | Nicholas et al. | |
| 8,551,076 B2 | 10/2013 | Duval et al. | |
| 8,561,871 B2 | 10/2013 | Rajappa et al. | |
| 8,623,000 B2 | 1/2014 | Humayun et al. | |
| 8,632,463 B2 | 1/2014 | Drinan et al. | |
| 8,647,258 B2 | 2/2014 | Aranyi et al. | |
| 8,657,174 B2 | 2/2014 | Yates et al. | |
| 8,696,552 B2 | 4/2014 | Whitman | |
| 8,708,213 B2 | 4/2014 | Shelton, IV et al. | |
| 8,806,973 B2 | 8/2014 | Ross et al. | |
| 8,851,355 B2 | 10/2014 | Aranyi et al. | |
| 8,858,571 B2 | 10/2014 | Shelton, IV et al. | |
| 2003/0038938 A1 | 2/2003 | Jung et al. | |
| 2003/0130677 A1 | 7/2003 | Whitman et al. | |
| 2004/0133189 A1 | 7/2004 | Sakurai | |
| 2004/0176751 A1 | 9/2004 | Weitzner et al. | |
| 2005/0125027 A1 | 6/2005 | Knodel et al. | |
| 2005/0131442 A1 | 6/2005 | Yachia et al. | |
| 2006/0278680 A1 | 12/2006 | Viola et al. | |
| 2007/0023477 A1 | 2/2007 | Whitman et al. | |
| 2007/0055219 A1 | 3/2007 | Whitman et al. | |
| 2007/0152014 A1 | 7/2007 | Gillum et al. | |
| 2007/0175961 A1 | 8/2007 | Shelton et al. | |
| 2008/0110958 A1 | 5/2008 | McKenna et al. | |
| 2008/0188841 A1 | 8/2008 | Tomasello et al. | |
| 2008/0197167 A1 | 8/2008 | Viola et al. | |
| 2008/0255413 A1 | 10/2008 | Zemlok et al. | |
| 2009/0090763 A1 | 4/2009 | Zemlok et al. | |
| 2009/0145947 A1 | 6/2009 | Scirica et al. | |
| 2009/0171147 A1 | 7/2009 | Lee et al. | |
| 2009/0179063 A1 | 7/2009 | Milliman et al. | |
| 2009/0254094 A1 | 10/2009 | Knapp et al. | |
| 2010/0069942 A1 | 3/2010 | Shelton, IV | |
| 2010/0225073 A1 | 9/2010 | Porter et al. | |
| 2011/0077673 A1 | 3/2011 | Grubac et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0174099 A1 | 7/2011 | Ross et al. | |
| 2011/0204119 A1 | 8/2011 | McCuen | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0089131 A1 | 4/2012 | Zemlok et al. | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |

(56) References Cited

U.S. PATENT DOCUMENTS

| | | |
|---|---|---|
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |

FOREIGN PATENT DOCUMENTS

| | | |
|---|---|---|
| CN | 102 247 182 | 11/2011 |
| DE | 102008053842 A1 | 5/2010 |
| EP | 0 634 144 | 1/1995 |
| EP | 0 634 144 A1 | 1/1995 |
| EP | 0648476 A1 | 4/1995 |
| EP | 0686374 A2 | 12/1995 |
| EP | 0705571 A1 | 4/1996 |
| EP | 1723913 A1 | 11/2006 |
| EP | 1772105 A1 | 4/2007 |
| EP | 1813199 | 8/2007 |
| EP | 1813211 | 8/2007 |
| EP | 1943954 A2 | 7/2008 |
| EP | 1943956 A2 | 7/2008 |
| EP | 2 005 898 | 12/2008 |
| EP | 2 005 898 A2 | 12/2008 |
| EP | 2044890 A1 | 4/2009 |
| EP | 2 098 170 | 9/2009 |
| EP | 2 098 170 A2 | 9/2009 |
| EP | 2100562 A2 | 9/2009 |
| EP | 2165664 A2 | 3/2010 |
| EP | 2236098 | 10/2010 |
| EP | 2263568 | 12/2010 |
| EP | 2272443 A1 | 1/2011 |
| EP | 2316345 A1 | 5/2011 |
| EP | 2324776 A2 | 5/2011 |
| EP | 2329773 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 | 5/2013 |
| EP | 2606834 | 6/2013 |
| EP | 2676615 A2 | 12/2013 |
| ES | 2333509 A1 | 2/2010 |
| JP | 08-038488 | 2/1996 |
| JP | 2005-125075 A | 5/2005 |
| WO | 99/15086 A1 | 4/1999 |
| WO | WO 03/000138 | 1/2003 |
| WO | 03/030743 A2 | 4/2003 |
| WO | 03065916 A1 | 8/2003 |
| WO | 03090630 A2 | 11/2003 |
| WO | 2007016290 A2 | 2/2007 |
| WO | WO 2007/014355 | 2/2007 |
| WO | WO 2007/014355 A2 | 2/2007 |
| WO | 2007137304 A2 | 11/2007 |
| WO | WO 2009/039506 A1 | 3/2009 |
| WO | 2009/143092 A1 | 11/2009 |
| WO | 2009149234 A1 | 12/2009 |
| WO | WO 2011/108840 | 9/2011 |
| WO | 2012040984 A1 | 4/2012 |

OTHER PUBLICATIONS

European Search Report corresponding to European Application EP 13 17 5479.8, mailed on Oct. 10, 2013; 7 pages.

European Search Report corresponding to European Application EP 10 25 2037.6; completed Mar. 1, 2011 and mailed Mar. 9, 2011; 3 pages.

Extended European Search Report corresponding to EP No. 11 17 8021.9, mailed Jun. 4, 2013; (3 pp).

Extended European Search Report corresponding to EP No. 13 16 3033.7, completed Jun. 27, 2013 and mailed Jul. 15, 2013; (8 pp).

Extended European Search Report corresponding to EP No. 12 18 6177.7, completed Aug. 14, 2013 and mailed Aug. 23, 2013; (8 pp).

Partial European Search Report corresponding to EP No. 13 17 1742.3, completed Sep. 17, 2013 and mailed Sep. 25, 2013; (8 pp).

Partial European Search Report corresponding to EP No. 13 17 2400.7, completed Sep. 18, 2013 and mailed Oct. 1, 2013; (7 pp).

Extended European Search Report corresponding to EP No. 13 17 5475.6, completed Sep. 23, 2013 and mailed Oct. 1, 2013; (8 pp).

Extended European Search Report corresponding to EP No. 13 17 5478.0, completed Sep. 24, 2013 and mailed Oct. 2, 2013; (6 pp).

Extended European Search Report corresponding to EP No. 13 17 5479.8, completed Sep. 27, 2013 and mailed Oct. 10, 2013; (7 pp).

Partial Extended European Search Report corresponding to EP 13 17 5477.2, completed Oct. 7, 2013 and mailed Oct. 15, 2013; (7 pp).

Extended European Search Report corresponding to EP No. 08 25 2703.7, completed Oct. 23, 2008 and mailed Oct. 31, 2008; (7 pp).

European search Report from Appl. No. 13177163.6 dated Nov. 15, 2013. (8 pp).

Extended European Search Report from EP Application No. 13172400.7 dated Jan. 21, 2014.

Extended European Search Report from EP Application No. 13189026.1 dated Jan. 31, 2014.

Extended European Search Report from Application No. EP 13177163.6 dated Feb. 6, 2014.

Extended European Search Report from Application No. EP 13175477.2 dated Feb. 6, 2014.

Extended European Search Report from Application No. EP 13169998.5 dated Feb. 24, 2014.

Extended European Search Report corresponding to EP 13176805.3, dated Nov. 4, 2013.

Extended European Search Report from Application No. EP 13171742.3 dated Jan. 3, 2014.

* cited by examiner

QUICK CONNECT ASSEMBLY FOR USE BETWEEN SURGICAL HANDLE ASSEMBLY AND SURGICAL ACCESSORIES

CROSS-REFERENCE TO RELATED APPLICATION

The present application is a Continuation-in-Part application claiming the benefit of and priority to U.S. patent application Ser. No. 13/484,975, filed on May 31, 2012, which is a Continuation-in-Part Application claiming the benefit of and priority to U.S. patent application Ser. No. 13/331,047, filed on Dec. 20, 2011 now U.S. Pat. No. 8,968,276, which is a Continuation-in-Part Application claiming the benefit of and priority to U.S. patent application Ser. No. 12/946,082, filed on Nov. 15, 2010 now U.S. Pat. No. 8,806,973, which claims the benefit of and priority to each of U.S. Provisional Application Ser. No. 61/308,045, filed on Feb. 25, 2010, and U.S. Provisional Application Ser. No. 61/265,942, filed on Dec. 2, 2009, the entire content of each of which being incorporate herein by reference.

U.S. patent application Ser. No. 13/331,047, filed on Dec. 20, 2011, is a Continuation-in-Part Application claiming the benefit of and priority to U.S. patent application Ser. No. 12/758,900, filed on Apr. 13, 2010, which is a Continuation-in-Part Application claiming the benefit of and priority to U.S. patent application Ser. No. 12/622,827, filed on Nov. 20, 2009, the entire content of each of which being incorporated herein by reference.

U.S. patent application Ser. No. 13/331,047, filed on Dec. 20, 2011, is a Continuation-in-Part Application claiming the benefit of and priority to U.S. patent application Ser. No. 13/089,672, filed on Apr. 19, 2011 now U.S. Pat. No. 8,342,379, which is a Divisional Application claiming the benefit of and priority to U.S. patent application Ser. No. 12/235,362, filed on Sep. 22, 2008 (now U.S. Pat. No. 7,963,433), which claims the benefit of and priority to U.S. Provisional Patent Application Ser. No. 60/974,267, filed on Sep. 21, 2007, the entire content of each of which being incorporated herein by reference.

U.S. patent application Ser. No. 13/331,047, filed on Dec. 20, 2011, is a Continuation-in-Part Application claiming the benefit of and priority to U.S. patent application Ser. No. 13/089,473, filed on Apr. 19, 2011, which is a Divisional Application claiming the benefit of and priority to U.S. patent application Ser. No. 12/235,362, filed on Sep. 22, 2008 (now U.S. Pat. No. 7,963,433), which claims the benefit of and priority to U.S. Provisional Patent Application Ser. No. 60/974,267, filed on Sep. 21, 2007, the entire content of each of which being incorporated herein by reference.

U.S. patent application Ser. No. 13/331,047, filed on Dec. 20, 2011, is a Continuation-in-Part Application claiming the benefit of and priority to U.S. patent application Ser. No. 13/090,286, filed on Apr. 20, 2011 now U.S. Pat. No. 8,272,554, which is a Divisional Application claiming the benefit of and priority to U.S. patent application Ser. No. 12/235,362, filed on Sep. 22, 2008 (now U.S. Pat. No. 7,963,433), which claims the benefit of and priority to U.S. Provisional Patent Application Ser. No. 60/974,267, filed on Sep. 21, 2007, the entire content of each of which being incorporated herein by reference.

BACKGROUND

1. Technical Field

The present disclosure relates to surgical devices. More specifically, the present disclosure relates to electromechanical surgical devices including quick connect/disconnect arrangements for quickly and efficiently connecting and disconnecting surgical accessories thereto.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary powered drive systems for operating and/or manipulating the surgical device. In many instances the surgical devices include a powered handle assembly, which is reusable, and a disposable end effector or the like that is selectively connected to the powered handle assembly prior to use and then disconnected from the end effector following use in order to be disposed of or in some instances sterilized for re-use.

Many of the existing end effectors for use with many of the existing powered surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, a need exists for adapters and/or adapter assemblies to interface between and interconnect the linear driven end effectors with the powered rotary driven surgical devices and/or handle assemblies.

It is desirable for these adapters and/or adapter assemblies to selectively connect/re-connect with the underlying powered surgical devices and/or handle assemblies via a quick-connect/quick-disconnect mechanism.

Accordingly, a need exists for adapters and/or adapter assemblies, and underlying powered surgical devices and/or handle assemblies including complementary quick-connect/quick-disconnect mechanisms.

SUMMARY

The present disclosure relates to electromechanical surgical devices including quick connect/disconnect arrangements for quickly and efficiently connecting and disconnecting surgical accessories thereto.

According to an aspect of the present disclosure, a handheld electromechanical surgical device is provided and configured to selectively connect with a surgical accessory, wherein the surgical accessory includes a cylindrical coupling assembly defining an annular groove formed in an outer surface thereof. The electromechanical surgical device includes a device housing defining a connecting portion for selectively receiving the coupling assembly of the surgical accessory. The connecting portion includes an annular wall defining a cylindrical recess dimensioned to receive the coupling assembly of the surgical accessory; a collar slidably supported about the annular wall, wherein the collar is slidable between a first position and a second position; and at least one socket member interposed between the annular wall and the collar, wherein each socket member is slidably supported in the annular wall. Each socket member includes a first fixed state wherein each socket member projects into the cylindrical recess of the annular wall; and a second movable state wherein each socket member is free to not project into the cylindrical recess of the annular wall. Wherein, when the collar is in the first position, the collar acts on each socket member to maintain each socket in the first state. Wherein, when the collar is in the second position, each socket member is free to move to the second state.

The collar may be spring biased to the first position.

Each socket member may be in registration with the annular groove of the surgical accessory when the surgical accessory is connected to the electromechanical surgical device.

Each socket member may at least partially enter the annular groove of the surgical accessory when the surgical accessory is connected to the electromechanical surgical device and when the collar is in the first position.

In use, when the surgical accessory is connected to the electromechanical surgical device, and when the collar is in the first position, the surgical accessory is prevented from disconnection from the electromechanical surgical device.

The collar may include a camming ring located along an inner surface thereof, wherein the camming ring acts on each socket member when the camming member is in the first position.

The surgical accessory may be connectable to the electromechanical surgical device when the collar is in the second position.

The surgical accessory may be not connectable to the electromechanical surgical device when the collar is in the first position.

The surgical accessory may be inhibited from disconnection from the electromechanical surgical device when the surgical accessory is connected to the electromechanical surgical device and when the collar is in the first position.

The first position of the collar may be a distally advanced position. The second position of the collar may be a proximally retracted position.

The at least one socket member may include three socket members radially evenly spaced around the annular wall of the connecting portion.

The connecting portion may further include an alignment nub projecting radially into the cylindrical recess, wherein the alignment nub is dimensioned to enter an alignment slot provided on an outer surface of the cylindrical coupling assembly of the surgical accessory.

The camming ring may be secured to the inner surface thereof.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
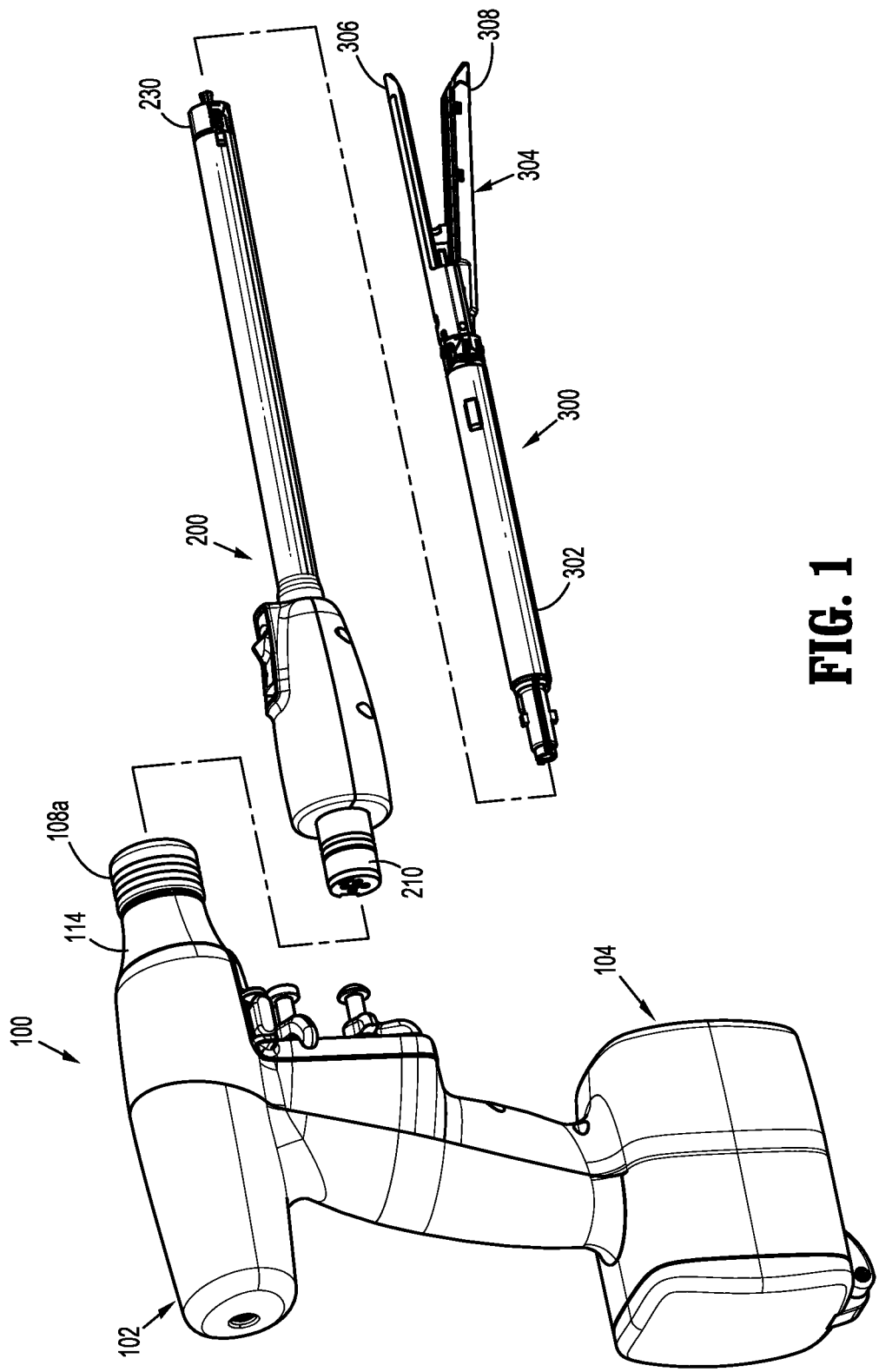
FIG. 1 is a perspective view, with parts separated, of a surgical device and adapter assembly, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

As illustrated in FIG. 1, surgical device 100 is configured for selective connection with a surgical accessory in the form or an adapter assembly 200, and, in turn, adapter assembly 200 is configured for selective connection with an end effector or single use loading unit 300.

Figure 2:
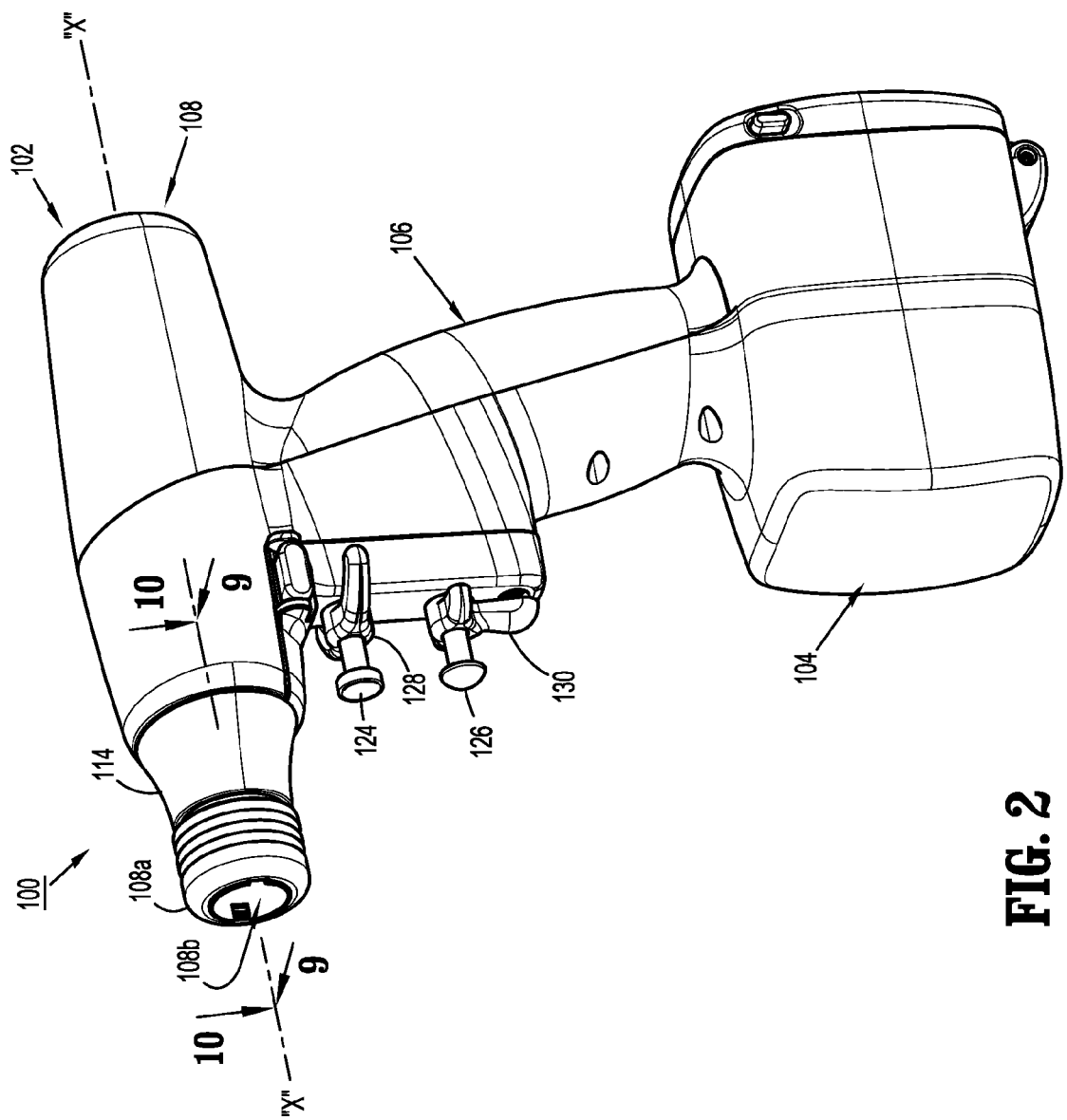
FIG. 2 is a perspective view of the surgical device of FIG. 1.

As illustrated in FIGS. 1 and 2, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section that is integrally formed with and extending from the lower portion 104, and a proximal half-section connectable to the distal half-section by a plurality of fasteners. When joined, the distal and proximal half-sections define a handle housing 102 having a cavity therein in which a circuit board (not shown) and a drive mechanism (not shown) are situated.

Figure 3:
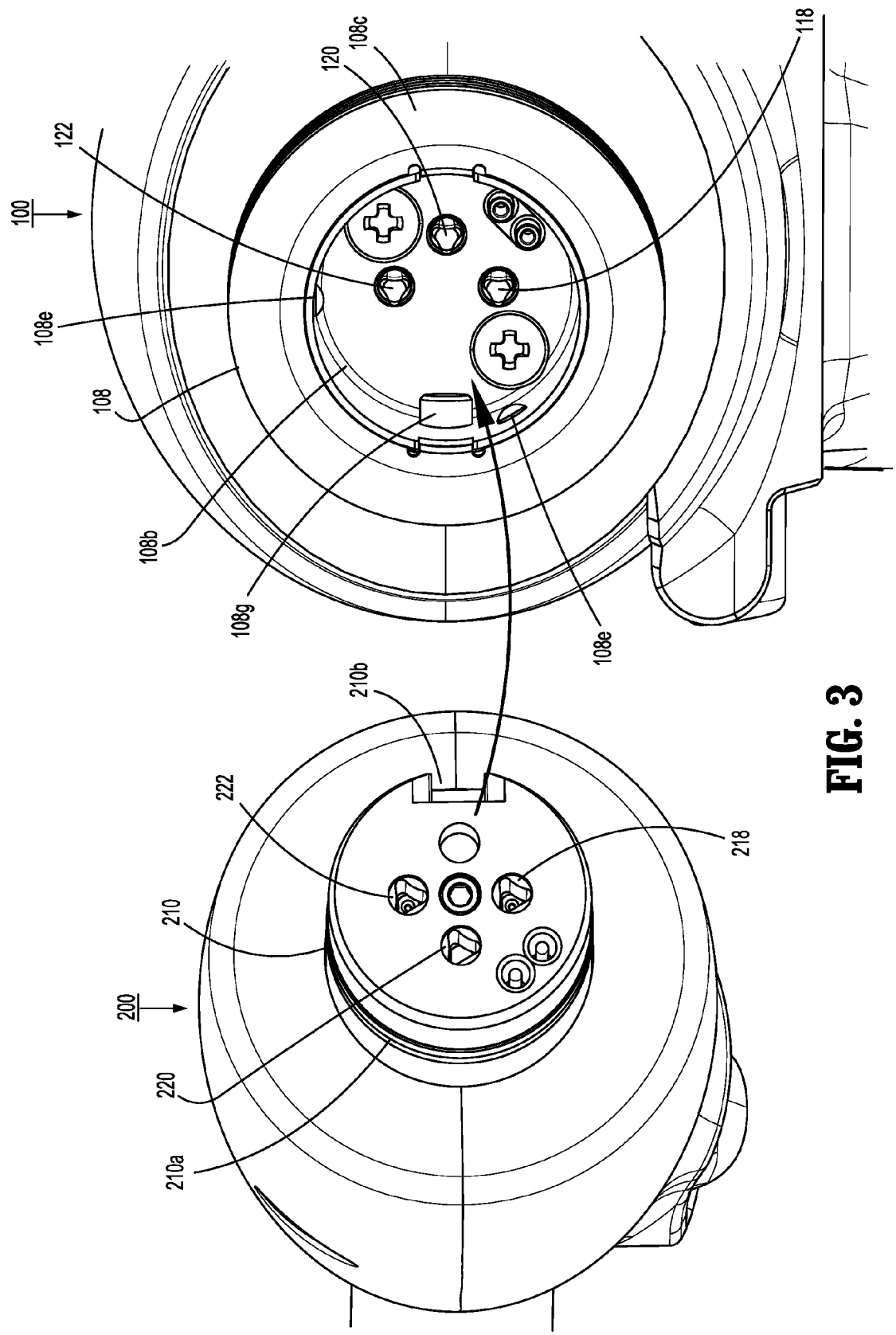
FIG. 3 is a perspective view of the connecting ends of each of the surgical device and the adapter assembly, illustrating a connection therebetween.
Figure 4:
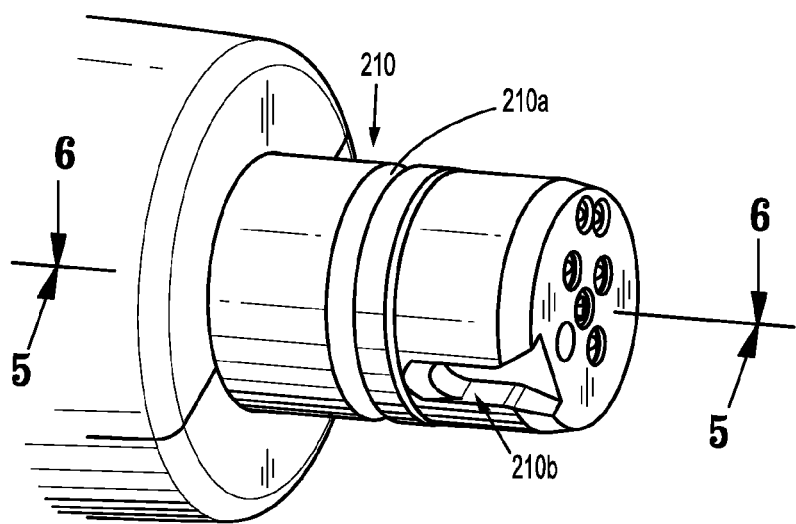
FIG. 4 is a rear, perspective view of a drive coupling housing of the adapter assembly of FIGS. 1-3.
Figure 5:
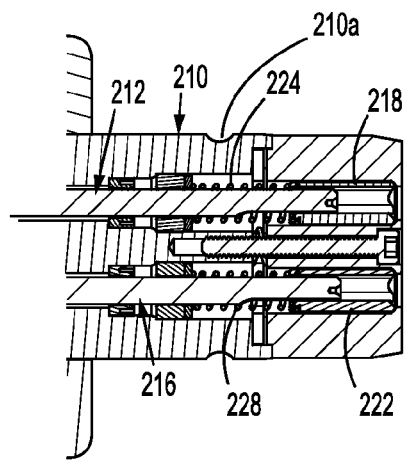
FIG. 5 is a cross-sectional view of the drive coupling housing of FIG. 4, as taken through 5-5 of FIG. 4.
Figure 6:
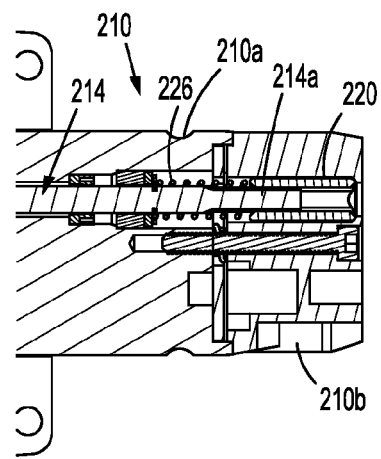
FIG. 6 is a cross-sectional view of the drive coupling housing of FIG. 4, as taken through 6-6 of FIG. 4.
Figure 7:
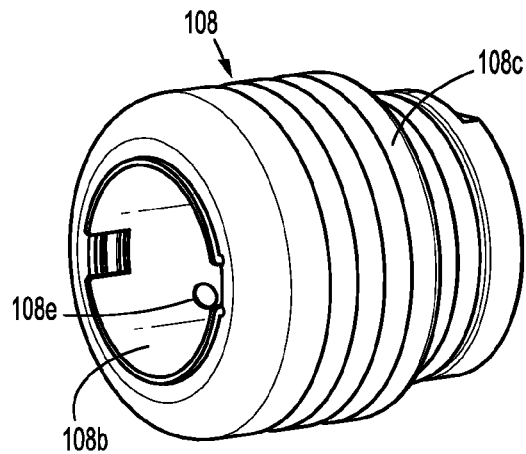
FIG. 7 is an enlarged, perspective view of a connecting portion of the surgical device of FIGS. 1-3.
Figure 8:
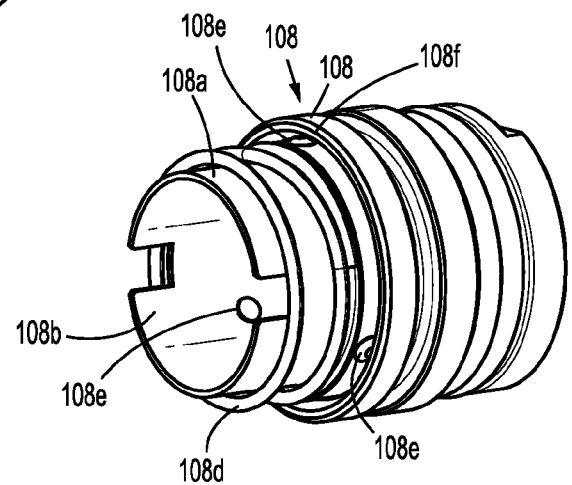
FIG. 8 is an enlarged perspective view with a collar of the connecting portion of FIG. 7 removed.
Figure 9:
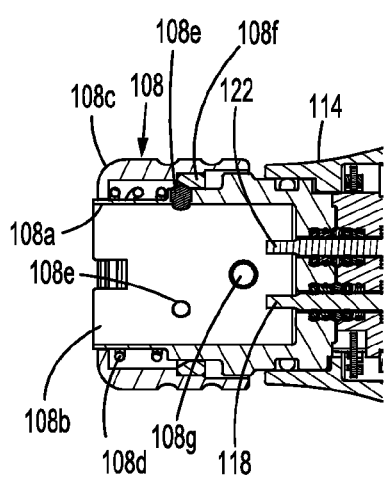
FIG. 9 is a cross-sectional view of the connecting portion of FIGS. 1-3 and 7-8, as taken through 9-9 of FIG. 2.
Figure 10:
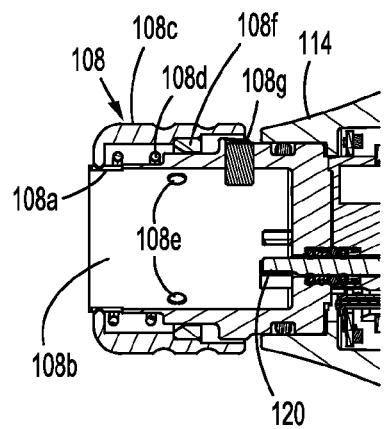
FIG. 10 is a cross-sectional view of the connecting portion of FIGS. 1-3 and 7-8, as taken through 10-10 of FIG. 2.

With reference to FIGS. 1-3, the distal half-section of upper housing portion 108 defines a nose or connecting portion 108a. A nose cone 114 is supported on nose portion 108a of upper housing portion 108. Nose cone 114 is fabricated from a transparent material. An illumination member (not shown) is disposed within nose cone 114 such that the illumination member is visible therethrough. The illumination member may be in the form of a light emitting diode printed circuit board (LED PCB). The illumination member may be configured to illuminate multiple colors with a specific color pattern being associated with a unique discrete event.

Upper housing portion 108 of handle housing 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively move tool assembly 304 of end effector 300 (see FIGS. 1 and 14) relative to proximal body portion 302 of end effector 300, to rotate end effector 300 about a longitudinal axis "X" (see FIG. 2) relative to handle housing 102, to move anvil assembly 306 relative to cartridge assembly 308 of end effector 300, and/or to fire a stapling and cutting cartridge within cartridge assembly 308 of end effector 300.

As illustrated in FIGS. 1-3, and as mentioned above, the distal half-section of upper housing portion 108 defines a connecting portion 108a configured to accept a corresponding drive coupling assembly 210 of adapter assembly 200.

Figure 13:
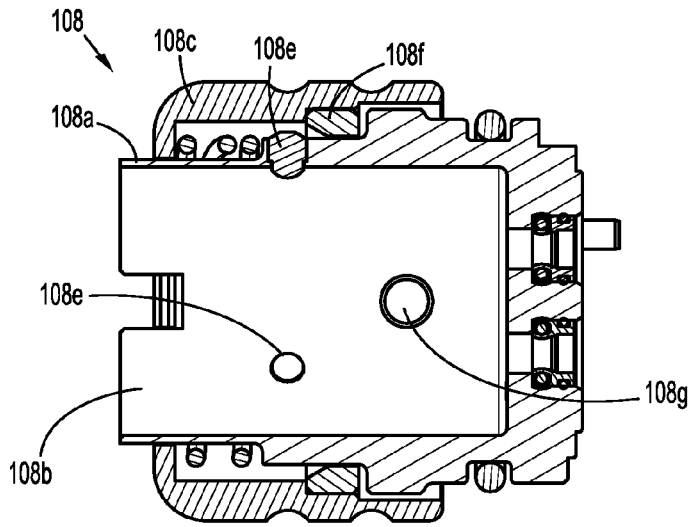
FIG. 13 is an enlarged view of the connecting portion, as shown in FIG. 9, illustrating the collar of the connecting portion in a retracted position.

As illustrated in FIGS. 2, 3 and 7-13, connecting portion 108a of surgical device 100 defines a cylindrical recess 108b that receives a drive coupling assembly 210 of adapter assembly 200 when adapter assembly 200 is mated to surgical device 100. Connecting portion 108a supports a collar 108c therearound, wherein collar 108c is slidable between a first or advanced position and a second or retracted position. When collar 108c is in the advanced position, as seen in FIGS. 9-12, drive coupling assembly 210 of adapter assembly 200 may not be connected to surgical device 100, or drive coupling assembly 210 of adapter assembly 200 is secured to surgical device 100 and can not be disconnected from surgical device 100. When collar 108c is in the retracted position, as seen in FIG. 13, drive coupling assembly 210 of adapter assembly 200 may be inserted into or withdrawn from cylindrical recess 108b of connecting portion 108a of surgical device 100.

In accordance with the present disclosure, it is envisioned that the direction of movement of collar 108c for performing the functions described herein, may be reversed, without departing from the principles of the present invention.

As seen in FIGS. 8-12, collar 108c is biased to the advanced position by a biasing member 108d, such as, for example, a coil spring or the like. As seen in FIGS. 8-12, biasing member 108d is interposed between connecting portion 108a and collar 108c.

Turning now to FIGS. 3 and 7-13, connecting portion 108a supports at least one (preferably three radially evenly spaced) socket members 108e interposed between connecting portion 108a and collar 108c. In particular, each socket member 108e is supported in an annular wall of connecting portion 108a. Each socket member 108e has a first state when collar 108c is in the advanced position, wherein each socket member 108e projects into cylindrical recess 108b of connecting portion 108a, wherein each socket member 108e blocks or inhibits connection of drive coupling assembly 210 of adapter assembly 200 to surgical device 100, or each socket member 108e engages drive coupling assembly 210 of adapter assembly 200 and secure adapter assembly 200 to surgical device 100.

Each socket member 108e has a second state when collar 108c is in the retracted position, wherein each socket member 108e is free to move radially outward and permit insertion and/or removal of drive coupling assembly 210 of adapter assembly 200 from cylindrical recess 108b of connecting portion 108a of surgical device 100.

As seen in FIGS. 8-13, collar 108c includes a camming ring 108f supported on or integrally formed in an inner surface of collar 108c. Camming ring 108f is configured and shaped such that, as seen in FIGS. 9-12, when collar 108c is in the advanced position each socket member 108e is held in the first state, and, as seen in FIG. 13, when collar 108c is in the retracted position each socket member 108e is free to move to the second state.

Where camming ring 108f is provided herein as a separate member secured to collar 108c, it is contemplated that camming ring 108f may be press-fit into collar 108c, or that camming ring 108f may be secured to collar 108c by welding, adhering, fastening, threading features, roll/press pins, snap features, snap/retaining rings, etc.

As seen in FIGS. 3-6, connecting portion 108a houses three rotatable drive connectors 118, 120, 122. As seen in particular in FIG. 3, when adapter assembly 200 is mated to surgical device 100, each of rotatable drive connectors 118, 120, 122 of surgical device 100 couples with a corresponding rotatable connector sleeve 218, 220, 222 of adapter assembly 200. (see FIG. 3). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter assembly 200.

The mating of drive connectors 118, 120, 122 of surgical device 100 with connector sleeves 218, 220, 222 of adapter assembly 200 allows rotational forces to be independently transmitted via each of the three respective connector interfaces. The drive connectors 118, 120, 122 of surgical device 100 are configured to be independently rotated by the drive mechanism. In this regard, a function selection module of the drive mechanism selects which drive connector or connectors 118, 120, 122 of surgical device 100 is to be driven by an input drive component of the drive mechanism.

Since each of drive connectors 118, 120, 122 of surgical device 100 has a keyed and/or substantially non-rotatable interface with respective connector sleeves 218, 220, 222 of adapter assembly 200, when adapter assembly 200 is coupled to surgical device 100, rotational force(s) are selectively transferred from the drive mechanism of surgical device 100 to adapter assembly 200.

The selective rotation of drive connector(s) 118, 120 and/or 122 of surgical device 100 allows surgical device 100 to selectively actuate different functions of end effector 300. As will be discussed in greater detail below, selective and independent rotation of first drive connector 118 of surgical device 100 corresponds to the selective and independent opening and closing of tool assembly 304 of end effector 300, and driving of a stapling/cutting component of tool assembly 304 of end effector 300. Also, the selective and independent rotation of second drive connector 120 of surgical device 100 corresponds to the selective and independent articulation of tool assembly 304 of end effector 300 transverse to longitudinal axis "X" (see FIG. 2). Additionally, the selective and independent rotation of third drive connector 122 of surgical device 100 corresponds to the selective and independent rotation of end effector 300 about longitudinal axis "X" (see FIG. 2) relative to handle housing 102 of surgical device 100.

As illustrated in FIGS. 1 and 2, handle housing 102 supports a pair of finger-actuated control buttons 124, 126 and rocker devices 128, 130.

Actuation of first control button 124 causes tool assembly 304 of end effector 300 to close and/or a stapling/cutting cartridge within tool assembly 304 of end effector 300 to fire.

Actuation of rocker device 128 in a first direction causes tool assembly 304 to articulate relative to body portion 302 in a first direction, while actuation of rocker device 128 in an opposite, e.g., second, direction causes tool assembly 304 to articulate relative to body portion 302 in an opposite, e.g., second, direction.

Actuation of control button 126 causes tool assembly 304 of end effector 300 to open.

Actuation of rocker device 130 causes end effector 300 to rotate relative to handle housing 102 of surgical device 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As illustrated in FIGS. 1-3, surgical device 100 is configured for selective connection with adapter assembly 200, and, in turn, adapter assembly 200 is configured for selective connection with end effector 300.

Figure 11:
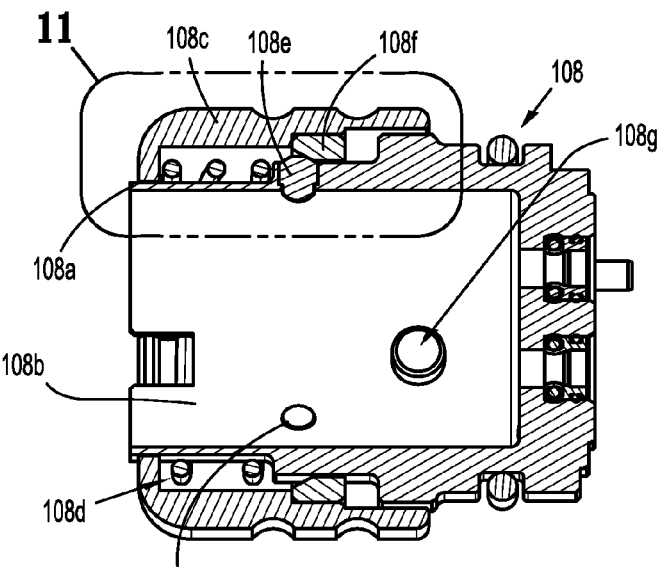
FIG. 11 is an enlarged view of the connecting portion, as shown in FIG. 9, illustrating the collar of the connecting portion in an advanced position.
Figure 12:
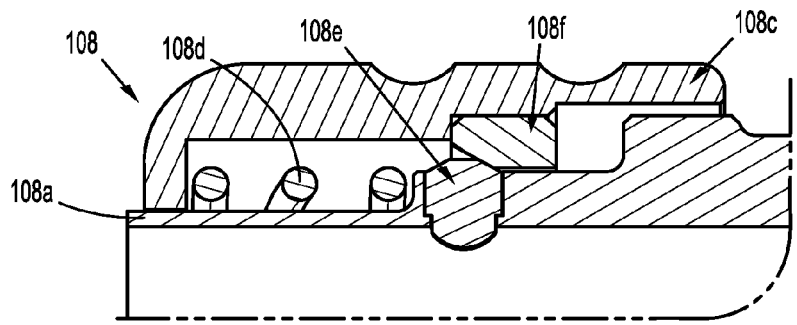
FIG. 12 is an enlarged view of the indicated area of detail of FIG. 11.

Adapter assembly 200 is configured to convert a rotation of either of drive connectors 120 and 122 of surgical device 100 into axial translation useful for operating a drive assembly 360 and an articulation link 366 of end effector 300, as illustrated in FIG. 11.

Adapter assembly 200 may include a first drive transmitting/converting assembly for interconnecting third rotatable drive connector 122 of surgical device 100 and a first axially translatable drive member of end effector 300, wherein the first drive transmitting/converting assembly converts and transmits a rotation of third rotatable drive connector 122 of surgical device 100 to an axial translation of the first axially translatable drive assembly 360 (see FIG. 14) of end effector 300 for firing.

Adapter assembly 200 may include a second drive transmitting/converting assembly for interconnecting second rotatable drive connector 120 of surgical device 100 and a second axially translatable drive member of end effector 300, wherein the second drive transmitting/converting assembly converts and transmits a rotation of second rotatable drive connector 120 of surgical device 100 to an axial translation of articulation link 366 (see FIG. 14) of end effector 300 for articulation.

Turning now to FIGS. 4-7, adapter assembly 200 includes a knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, that outer tube is passable through a typical trocar port, cannula or the like. Knob housing 202 is dimensioned to not enter the trocar port, cannula of the like.

Knob housing 202 is configured and adapted to connect to connecting portion 108*a* of upper housing portion 108 of the distal half-section of surgical device 100.

As seen in FIGS. 1 and 3-6, adapter assembly 200 includes a surgical device drive coupling assembly 210 at a proximal end thereof and to an end effector coupling assembly 230 at a distal end thereof. Drive coupling assembly 210 has a cylindrical profile and includes an annular groove 210*a* formed in an outer surface thereof. Annular groove 210*a* is configured and dimensioned to selectively receive each socket member 108*e* therein, when adapter assembly 200 is connected to surgical device 100.

Drive coupling assembly 210 rotatably supports a first rotatable proximal drive shaft 212, a second rotatable proximal drive shaft 214, and a third rotatable proximal drive shaft 216 therein. Drive coupling assembly 210 rotatably supports first, second and third connector sleeves 218, 220 and 222, respectively. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

With reference to FIGS. 1-13, a method of connecting adapter assembly 200 to surgical device 100 is discussed herein. As seen in FIG. 13, in order to connect adapter assembly 200 to surgical device 100, collar 108*c* of connecting portion 108*a* of surgical device 100 is moved to the retracted position. With collar 108*c* in the retracted position, and with each socket member 108*e* in the second state, drive coupling assembly 210 may be freely inserted into cylindrical recess 108*b* of connecting portion 108*a* of surgical device 100. When drive coupling assembly 210 is fully and properly inserted into cylindrical recess 108*b* of connecting portion 108*a* of surgical device 100, annular groove 210*a* of drive coupling assembly 210 is in alignment or registration with each socket member 108*e* of connecting portion 108*a* of surgical device 100.

With drive coupling assembly 210 fully and properly inserted into cylindrical recess 108*b* of connecting portion 108*a* of surgical device 100, and annular groove 210*a* of drive coupling assembly 210 in alignment or registration with each socket member 108*e* of connecting portion 108*a* of surgical device 100, collar 108*c* of connecting portion 108*a* of surgical device 100 is moved to the advanced position. As collar 108*c* of connecting portion 108*a* of surgical device 100 is moved to the advanced position, as seen in FIGS. 7-13, camming ring 108*f* of collar 108*c* acts on each socket member 108*e* to move each socket member 108*e* to the first state such that each socket member 108*e* is disposed and held in annular groove 210*a* of drive coupling assembly 210 to secure adapter assembly 200 to surgical device 100.

As seen in FIG. 13, in order to disconnect adapter assembly 200 from surgical device 100, collar 108*c* of connecting portion 108*a* of surgical device 100 is moved from the advanced position to the retracted position. When collar 108*c* is moved from the advanced position to the retracted position, each socket member 108*e* is transitioned from the first state to the second state, to thereby permit disconnection of drive coupling assembly 210 from cylindrical recess 108*b* of connecting portion 108*a* of surgical device 100.

As collar 108*c* of connecting portion 108*a* of surgical device 100 is moved to the retracted position, camming ring 108*f* of collar 108*c* disengages from each socket member 108e to transition each socket member 108e from the first state to the second state, whereby, as shaft assembly 200 is separated from surgical device 100, each socket member 108e is withdrawn from annular groove 210a of drive coupling assembly 210 to permit adapter assembly 200 to disconnect from surgical device 100.

As seen in FIGS. 3-13, surgical device 100 and adapter assembly 200 may include rotational alignment features associated therewith in order to appropriately clock and angularly align the surgical device 100 and adapter assembly 200 to each other during connection. Particularly, surgical device 100 may include an alignment nub 108g projecting into cylindrical recess 108b of connecting portion 108a, and adapter assembly 200 may include a longitudinally extending slot 210b formed in an outer surface of drive coupling assembly 210, wherein slot 210b extends through a proximal-most surface of drive coupling assembly 210. In this manner, alignment nub 108g of surgical device 100 must be angularly and axially aligned with slot 210b of adapter assembly 200 in order for surgical device 100 and adapter assembly 200 to be properly connected to one another.

In an embodiment, it is contemplated that collar 108c of surgical device 100 may include friction or grip increasing features, such as, for example, knurls, ribs or grooves formed in an outer surface thereof to minimize slipping and/or improve a gripability of collar 108c by an end user.

It is contemplated, in accordance with the present disclosure, that in a reusable, quick-connect mechanism, or in a mechanism that will undergo repeated insertion and removal, that the materials of each socket member 108e and the materials of drive coupling assembly 210 (defining annular groove 210a), are selected so as to assign one of these members as being a sacrificial wear member (i.e., the member which will undergo the most wear). This is attained by controlling a hardness of the materials of construction and by selecting the particular materials of construction (whether metal or plastic).

Adapter assembly 200 includes a first, a second and a third drive transmitting/converting assembly, as mentioned above, disposed within handle housing 202 and outer tube 206. Each drive transmitting/converting assembly is configured and adapted to transmit or convert a rotation of a first, second and third drive connector 118, 120, 122 of surgical device 100 into axial translation of a drive bar of adapter assembly 200, to effectuate closing, opening, articulating and firing of end effector 300; or a rotation of adapter assembly 200.

In operation, when a button of surgical device 100 is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter assembly 200 and/or end effector 300.

Figure 15:
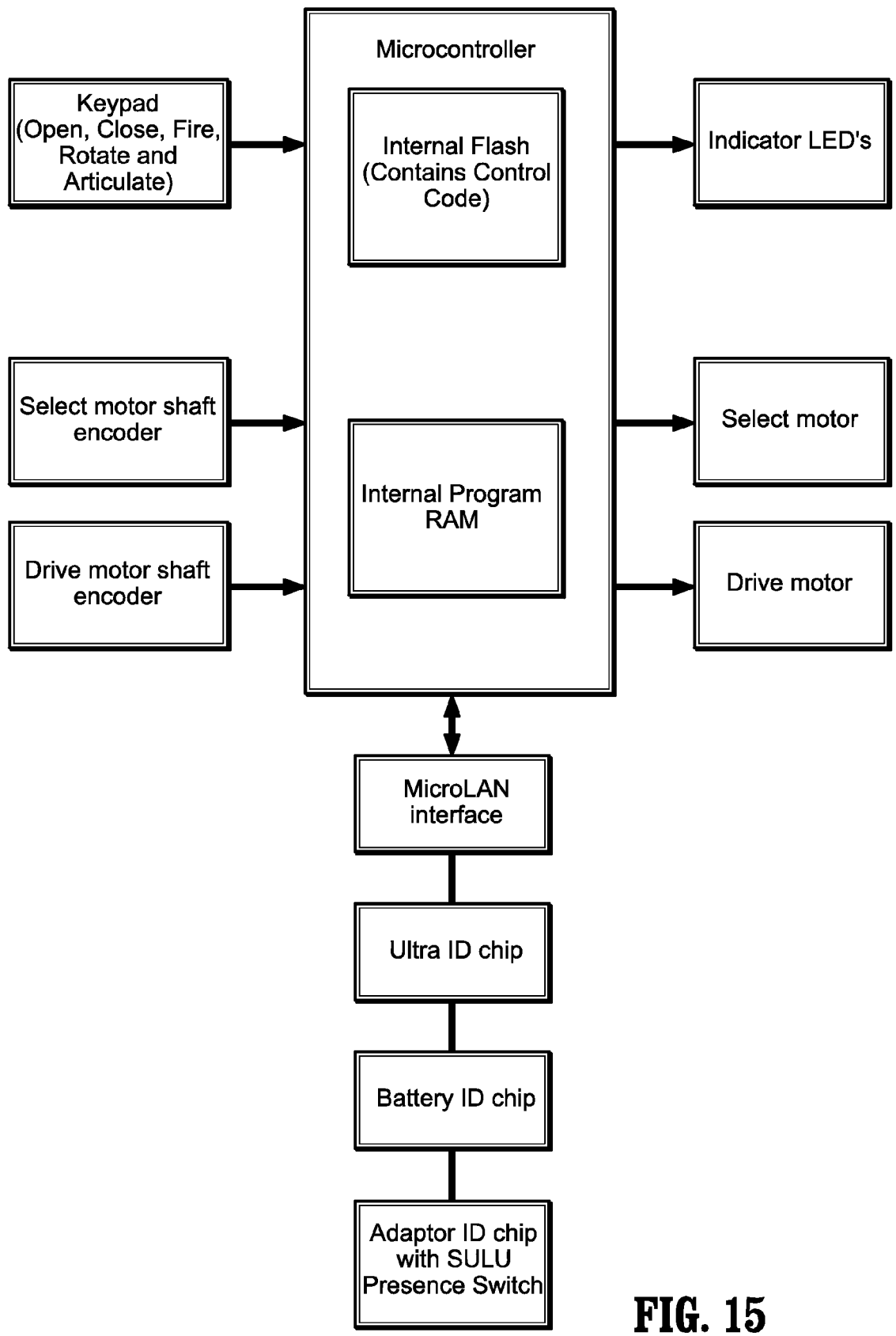
FIG. 15 is a schematic illustration of the outputs to the LED's; selection of motor (to select clamping/cutting, rotation or articulation); and selection of the drive motors to perform a function selected.

A high level electrical architectural view of the system is displayed in FIG. 15 and shows the connections to the various hardware and software interfaces. Inputs from presses of buttons 124, 126 and from motor encoders of the drive shaft are shown on the left side of FIG. 15. The microcontroller contains the device software that operates surgical device 100, adapter assembly 200 and/or end effector 300. The microcontroller receives inputs from and sends outputs to a MicroLAN, an Ultra ID chip, a Battery ID chip, and Adaptor ID chips.

The MicroLAN, the Ultra ID chip, the Battery ID chip, and the Adaptor ID chips control surgical device 100, adapter assembly 200 and/or end effector 300 as follows:

MicroLAN—Serial 1-wire bus communication to read/write system component ID information.

Ultra ID chip—identifies surgical device 100 and records usage information.

Battery ID chip—identifies the Battery 156 and records usage information.

Adaptor ID chip—identifies the type of adapter assembly 200, records the presence of an end effector 300, and records usage information.

The right side of the schematic illustrated in FIG. 15 indicates outputs to the LED's; selection of motor (to select clamping/cutting, rotation or articulation); and selection of the drive motors to perform the function selected.

Figure 14:
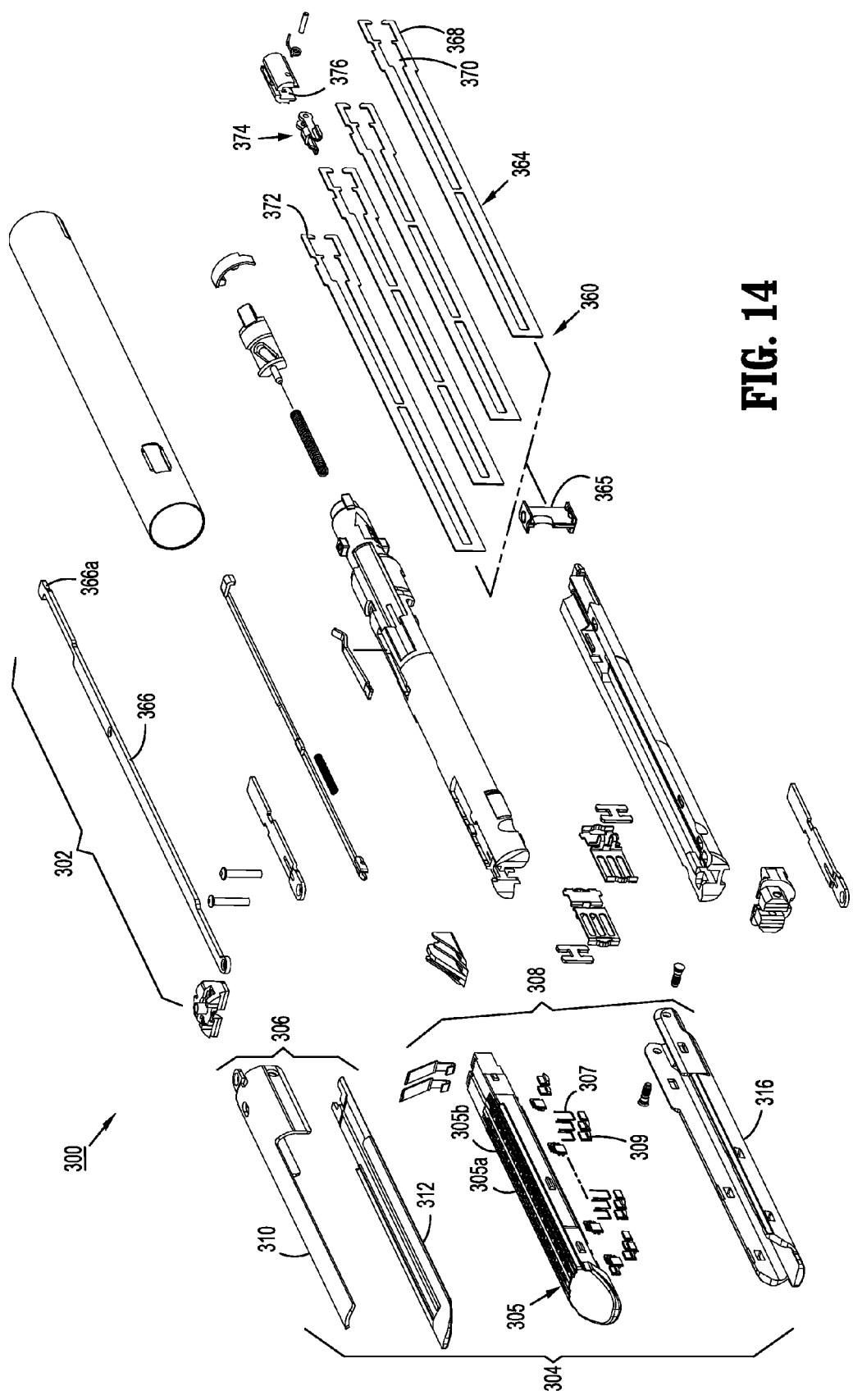
FIG. 14 is a perspective view, with parts separated, of an exemplary end effector for use with the surgical device and the adapter assembly of the present disclosure.

As illustrated in FIGS. 1 and 14, the end effector is designated as 300. End effector 300 is configured and dimensioned for endoscopic insertion through a cannula, trocar or the like. In particular, in the embodiment illustrated in FIGS. 1 and 14, end effector 300 may pass through a cannula or trocar when end effector 300 is in a closed condition.

End effector 300 includes a proximal body portion 302 and a tool assembly 304. Proximal body portion 302 is releasably attached to a distal coupling 230 of adapter assembly 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Proximal body portion 302 includes at least a drive assembly 360 and an articulation link 366.

Referring to FIG. 14, drive assembly 360 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376 which receives connection member 247 of drive tube 246 of first drive converter assembly 240 of adapter assembly 200 when end effector 300 is attached to distal coupling 230 of adapter assembly 200.

When drive assembly 360 is advanced distally within tool assembly 304, an upper beam of clamping member 365 moves within a channel defined between anvil plate 312 and anvil cover 310 and a lower beam moves over the exterior surface of carrier 316 to close tool assembly 304 and fire staples therefrom.

Proximal body portion 302 of end effector 300 includes an articulation link 366 having a hooked proximal end 366a which extends from a proximal end of end effector 300. Hooked proximal end 366a of articulation link 366 engages coupling hook 258c of drive bar 258 of adapter assembly 200 when end effector 300 is secured to distal housing 232 of adapter assembly 200. When drive bar 258 of adapter assembly 200 is advanced or retracted as described above, articulation link 366 of end effector 300 is advanced or retracted within end effector 300 to pivot tool assembly 304 in relation to a distal end of proximal body portion 302.

As illustrated in FIG. 14, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of surgical device 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject a single staple 307 therefrom for formation against anvil plate 312.

Reference may be made to U.S. Patent Publication No. 2009/0314821, filed on Aug. 31, 2009, entitled "TOOL ASSEMBLY FOR A SURGICAL STAPLING DEVICE," the entire content of which is incorporated herein by reference, for a detailed discussion of the construction and operation of end effector 300.

Reference may also be made to U.S. patent application Ser. No. 13/484,975, filed on May 31, 2012, entitled "HAND HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE", the entire content of which is incorporated herein by reference, for a detailed discussion of the construction and operation of any of the remaining components of surgical device 100, adapter assembly 200, and end effector 300.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A hand-held electromechanical surgical device configured to selectively connect with a surgical accessory, wherein the surgical accessory includes a cylindrical coupling assembly defining an annular groove formed in an outer surface thereof, the electromechanical surgical device, comprising:
   a device housing defining a connecting portion for selectively receiving the coupling assembly of the surgical accessory, the connecting portion includes:
      an annular wall defining a cylindrical recess dimensioned to receive the coupling assembly of the surgical accessory;
      a collar slidably supported about the annular wall, wherein the collar is slidable between a first position and a second position; and
      at least one socket member interposed between the annular wall and the collar, wherein each socket member is slidably supported in the annular wall, and wherein each socket member includes:
         a first fixed state wherein each socket member projects into the cylindrical recess of the annular wall; and
         a second movable state wherein each socket member is free to not project into the cylindrical recess of the annular wall;
   wherein, when the collar is in the first position, the collar acts on each socket member to maintain each socket in the first state; and
   wherein, when the collar is in the second position, each socket member is free to move to the second state, wherein the collar includes a discrete camming ring located along an inner surface thereof, wherein the discrete camming ring acts on each socket member when the collar is in the first position.

2. The electromechanical surgical device according to claim 1, wherein the collar is spring biased to the first position.

3. The electromechanical surgical device according to claim 1, wherein each socket member is in registration with the annular groove of the surgical accessory when the surgical accessory is connected to the electromechanical surgical device.

4. The electromechanical surgical device according to claim 3, wherein each socket member at least partially enters the annular groove of the surgical accessory when the surgical accessory is connected to the electromechanical surgical device and when the collar is in the first position.

5. The electromechanical surgical device according to claim 4, wherein when the surgical accessory is connected to the electromechanical surgical device, and when the collar is in the first position, the surgical accessory is prevented from disconnection from the electromechanical surgical device.

6. The electromechanical surgical device according to claim 1, wherein the surgical accessory is connectable to the electromechanical surgical device when the collar is in the second position.

7. The electromechanical surgical device according to claim 1, wherein the surgical accessory is not connectable to the electromechanical surgical device when the collar is in the first position.

8. The electromechanical surgical device according to claim 1, wherein the surgical accessory is inhibited from disconnection from the electromechanical surgical device when the surgical accessory is connected to the electromechanical surgical device and when the collar is in the first position.

9. The electromechanical surgical device according to claim 1, wherein the first position of the collar is a distally advanced position.

10. The electromechanical surgical device according to claim 1, wherein the second position of the collar is a proximally retracted position.

11. The electromechanical surgical device according to claim 1, wherein the at least one socket member includes three socket members radially evenly spaced around the annular wall of the connecting portion.

12. The electromechanical surgical device according to claim 1, wherein the connecting portion further includes an alignment nub projecting radially into the cylindrical recess, wherein the alignment nub is dimensioned to enter an alignment slot provided on an outer surface of the cylindrical coupling assembly of the surgical accessory.

13. The electromechanical surgical device according to claim 1, wherein the discrete camming ring is secured to the inner surface thereof.

* * * * *